United States Patent
Page et al.

(10) Patent No.: US 6,727,231 B1
(45) Date of Patent: Apr. 27, 2004

(54) URIDINE THERAPY FOR PATIENTS WITH ELEVATED PURINE LEVELS

(75) Inventors: Theodore M. Page, Carlsbad, CA (US); Deborah Brewer, Bethesda, MA (US); Charles D. Moseley, Arlington, VA (US)

(73) Assignee: Repligen Corporation, Needham, MA (US)

( * ) Notice: Subject to any disclaimer, the term of this patent is extended or adjusted under 35 U.S.C. 154(b) by 6 days.

(21) Appl. No.: 09/689,551

(22) Filed: Oct. 12, 2000

(51) Int. Cl.[7] .................... A01N 43/04; A61K 31/70
(52) U.S. Cl. ................ 514/50; 514/49; 536/28.5; 536/28.53
(58) Field of Search .............. 514/50, 49; 536/28.5, 536/28.53

(56) References Cited

U.S. PATENT DOCUMENTS

| | | | | |
|---|---|---|---|---|
| 4,960,759 A | 10/1990 | De Luca et al. | ............... | 514/50 |
| 5,470,838 A | 11/1995 | von Borstel et al. | ........... | 514/50 |
| 5,731,432 A | 3/1998 | Erion et al. | ................. | 540/568 |
| 5,962,459 A | 10/1999 | Piazza et al. | ............... | 514/269 |

FOREIGN PATENT DOCUMENTS

| | | | | |
|---|---|---|---|---|
| WO | WO 94/18200 | 8/1994 | ......... | C07D/487/04 |
| WO | WO 00/11952 | 3/2000 | .......... | A01N/43/04 |

OTHER PUBLICATIONS

Coleman et al., "Hyperuricosuria in autistic children; does this identify a subgroup of autism?", *The Autistic Syndromes*, Chapter 16 pp. 183–215 (1976).

Kaufman et al., "Urine uric acid to creatinine ratio–a screening test for inherited disorders of purine metabolism", *The Journal of PEDIATRICS*, vol. 73, No. 4, pp. 583–592 (1968).

Leyva et al., "Phase I and Pharmacokinetic Studies of High–Dose Uridine Intended for Rescue from 5–Fluorouracil Toxicity[1]", *Cancer Research*, vol. 44, pp. 5928–5933 (1984).

Liddle et al., "The Enzymatic Spectrophotometric Method For Determination of Uric Acid", *J. Lab & Clin. Med.*, vol. 54, No. 6, pp. 903–913 (1959).

Page et al., "Developmental disorder associated with increased cellular nucleotidase activity", *Proc. Natl. Acad. Sci. USA*, vol. 94, pp. 11601–11606 (1997).

Page et al., Purine metabolism abnormalities in a hyperuricosuric subclass of autism, *Biochimica et Biophysica Acta 61913*, pp. 1–6 (2000).

*Primary Examiner*—James O. Wilson
*Assistant Examiner*—Patrick Lewis
(74) *Attorney, Agent, or Firm*—Fish & Richardson P.C.

(57) ABSTRACT

The invention is based on the discovery that patients having elevated purine levels, e.g., individuals diagnosed with pervasive developmental disorders, such as autistic disorder, and/or neuromuscular disorders, can be treated with uridine compositions.

13 Claims, No Drawings

URIDINE THERAPY FOR PATIENTS WITH ELEVATED PURINE LEVELS

TECHNICAL FIELD

This invention relates to the diagnosis and treatment of disorders associated with elevated purine levels, such as pervasive developmental disorders.

BACKGROUND

A variety of grave disorders of human development are associated with elevated purine levels. Patients with these disorders may have seizures, transient ischemic attacks, and neurological and neuromuscular impairments such as ataxia and spasticity. In addition, such patients may exhibit profound developmental, behavioral, and psychological problems. For example, they may exhibit symptoms of Pervasive Developmental Disorder (PDD). PDD is a diagnostic category first used in the 1980s to describe a group of patients who typically exhibit one or more severe impairments including: reduced or absent social interaction, cognitive delay, attentional deficits, impaired learning, distorted sensory perception, deficient imaginative activity, and deficiency or absence of verbal and nonverbal communication skills. In addition, all have a limited number of interests and demonstrate activities that tend to be repetitive. The various types of PDD are typically diagnosed following the guidelines in the Diagnostic and Statistical Manual of Mental Disorders (DSM)(American Psychiatric Association, Washington, D.C., pages 66–71, 1994). The fourth edition of these guidelines, DSM-IV, identifies five separate disorders under the category of Pervasive Developmental Disorders: (1) Autistic Disorder, (2) Rett's Disorder, (3) Childhood Disintegrative Disorder, (4) Asperger's Disorder, and (5) Pervasive Developmental Disorder Not Otherwise Specified, or PDDNOS.

Autistic disorder or autism is a severely debilitating developmental disorder characterized by deficiency in verbal communication and socialization. In addition, children with autistic disorder typically have moderate to severe behavioral problems. Many children with autism also have mental retardation. Autism is generally diagnosed in children between the ages of 2 and 6, typically using the criteria established in DSM-IV ((APA, 1994, p. 70–71).

A child is diagnosed as having autistic disorder if the child fits into all of categories A, B, and C as follows.

A. A total of six (or more) items from (1), (2), and (3), with at least two from (1), and one each from (2) and (3):
  (1) qualitative impairment in social interaction, as manifested by at least two of the following: (a) marked impairment in the use of multiple nonverbal behaviors such as eye-to-eye gaze, facial expression, body postures, and gestures to regulate social interaction; (b) failure to develop peer relationships appropriate to developmental level; (c) a lack of spontaneous seeking to share enjoyment, interests, or achievements with other people (e.g., by a lack of showing, bringing, or pointing out objects of interest); and (d) lack of social or emotional reciprocity.
  (2) qualitative impairments in communication as manifested by at least one of the following: (a) delay in, or total lack of, the development of spoken language (not accompanied by an attempt to compensate through alternative modes of communication such as gesture or mime); (b) in individuals with adequate speech, marked impairment in the ability to initiate or sustain a conversation with others; (c) stereotyped and repetitive use of language or idiosyncratic language; and (d) lack of varied, spontaneous make-believe play or social imitative play appropriate to developmental level.
  (3) restricted repetitive and stereotyped patterns of behavior, interests, and activities, as manifested by at least one of the following: (a) encompassing preoccupation with one or more stereotyped and restricted patterns of interest that is abnormal either in intensity or focus; (b) apparently inflexible adherence to specific, nonfunctional routines or rituals; (c) stereotyped and repetitive motor mannerisms (e.g., hand or finger flapping or twisting, or complex whole-body movements); and (d) persistent preoccupation with parts of objects.

B. Delays or abnormal functioning in at least one of the following areas, with onset prior to age 3 years:
  (1) social interaction,
  (2) language as used in social communication, or
  (3) symbolic or imaginative play.

C. The disturbance is not better accounted for by Rett's Disorder or Childhood Disintegrative Disorder.

Asperger's Disorder, also referred to as Asperger's or Asperger's Syndrome, is a developmental disorder characterized by a lack of social skills; difficulty with social relationships; poor coordination and concentration; and a restricted range of interests, but normal intelligence and adequate language skills. Individuals with Asperger's Disorder do not possess a significant delay in language development, but they may have difficulty understanding certain aspects of conversation such as irony and humor. Asperger's patients tend to have an average or above average intelligence. A child is diagnosed with Asperger's Disorder if they meet the diagnostic criteria set forth in the DSM-IV in categories A through F as follows (APA, 1994, p. 77).

A. Qualitative impairment in social interaction, as manifested by at least two of the following:
  (1) marked impairment in the use of multiple nonverbal behaviors such as eye-to-eye gaze, facial expression, body postures, and gestures to regulate social interaction;
  (2) failure to develop peer relationships appropriate to developmental level;
  (3) a lack of spontaneous seeking to share enjoyment, interests, or achievements with other people (e.g., by a lack of showing, bringing, or pointing out objects of interest); and
  (4) lack of social or emotional reciprocity.

B. Restricted repetitive and stereotyped patterns of behavior, interests, and activities, as manifested by at least one of the following:
  (1) encompassing preoccupation with one or more stereotyped and restricted patterns of interest that is abnormal either in intensity or focus;
  (2) apparently inflexible adherence to specific, nonfunctional routines or rituals;
  (3) stereotyped and repetitive motor mannerisms (e.g., hand or finger flapping or twisting, or complex whole-body movements); and
  (4) persistent preoccupation with parts of objects.

C. The disturbance causes clinically significant impairment in social, occupational, or other important areas of functioning.

D. There is no clinically significant general delay in language (e.g., single words used by age 2 years, communicative phrases used by age 3 years).

E. There is no clinically significant delay in cognitive development or in the development of age-appropriate self-help skills, adaptive behavior (other than in social interaction), and curiosity about the environment in childhood.

F. Criteria are not met for another specific Pervasive Developmental Disorder, or Schizophrenia.

When an individual has several of the symptoms of the other specific PDDs, but does not quite meet all of the criteria or is not severely impaired, Pervasive Developmental Disorder Not Otherwise Specified (PDDNOS) may be diagnosed. Children with PDDNOS either (a) do not fully meet the criteria of symptoms clinicians use to diagnose any of the four specific types of PDD above, and/or (b) do not have the degree of impairment described in any of the above four PDD specific types.

Besides their developmental and behavioral problems, a significant subgroup of children diagnosed with autistic disorder, other PDDs, and/or neuromuscular symptoms, have also been shown to have an abnormal purine metabolism, as evidenced, for example, by hyperuricosuria, a condition in which the patient, e.g., a child, excretes an abnormally high level of uric acid in his or her urine than normal children and other autistic children. See, Page and Coleman, *Biochimica et Biophysica Acta*, 61913:1–6 (2000). Some of these patients also exhibit a marked abnormality of about a two to four-fold increase in de novo purine synthesis. A low purine diet, which lowers urate excretion, has been shown to improve the symptoms in some of these patients. In addition, some of these patients have benefited from the administration of allopurinol, a xanthine oxidase inhibitor that decreases production of uric acid.

In contrast to these hyperuricosuric patients, certain patients diagnosed with symptoms including developmental delay, seizures, ataxia, recurrent infections, speech deficit, and an unusual behavioral phenotype, have been shown to be hypouricosuric, that is, they excrete less than the average, normal amount of uric acid in their urine. A regimen of single oral doses of 1,000 mg/kg/day of uridine was found to reduce the symptoms in these hypouricosuric PDD patients, although the mechanism for the effectiveness of this treatment remains unclear. Page et al., *P.N.A.S., USA*, 94:11601–11606 (1997).

SUMMARY

The invention is based on the theory and demonstrated discovery that individuals who have elevated purine levels can be treated by uridine therapy. The individuals with elevated purine levels can also exhibit additional symptoms. For example, these patients can exhibit symptoms of PDD and/or symptoms of neuromuscular disorders such as ataxia, gross and fine motor coordination, seizures, and spasticity. Such patients may also have transient ischemic attacks and/or breathing disorders. The elevated purine levels can be evidenced by, e.g., hyperuricosuria, an elevated level of de novo purine synthesis, or a decreased adenine/guanine nucleotide ratio.

The invention includes diagnostic aspects. For example, the level of de novo purine synthesis in cells, e.g., in fibroblasts, is significantly increased in certain individuals, e.g., in individuals with autistic disorder, compared to levels in normal individuals. Consequently, a level of de novo purine synthesis above a certain range in patients, e.g., with autistic disorder, indicates that these patients can be treated with uridine compositions. Similarly, patients with a decreased ratio of adenine to guanine nucleotides in cellular assays can be treated with uridine compositions.

Thus, in general, the invention features a method of treating an individual having an elevated purine level (e.g., an individual who is hyperuricosuric, or who was hyperuricosuric as a child) by administering to the individual an effective amount of a uridine composition. The individual may have one or more symptoms of PDD, e.g., one or more symptoms of autistic disorder, or may have seizures, a neuromuscular disorder, or ataxia. For example, the amount of the uridine composition can be effective to improve one or more of the symptoms of PDD or one or more of the symptoms of autistic disorder. For example, the effective amount of the uridine composition can provide about 100 to 1500 mg, e.g., 100 to 250 mg, of uridine/kg of body weight/day. The uridine composition can be administered orally, for example, when the uridine composition includes uridine and a liquid ingestible carrier. In specific embodiments, the uridine composition can be or include triacetyl uridine.

In another aspect, the invention features a method of diagnosing an individual for elevated purine levels by obtaining a sample of cells from the individual; measuring a level of de novo purine synthesis in the cell sample; and comparing the level to a threshold level of at least 15.0 nmol/100 nmol/day. A level above the threshold level indicates that the individual has an elevated purine level. In this method, the threshold level can be 20 nmol/100 nmol/day. The individual may have one or more symptoms of PDD, or autistic disorder, or a neuromuscular disorder.

The invention also features a method of diagnosing an individual for elevated purine levels by obtaining a sample of cells from the individual; measuring a ratio of adenine to guanine nucleotides in the cell sample; and comparing the ratio to a threshold ratio of up to 6.38. A ratio below the threshold ratio indicates that the individual has an elevated purine level. For example, the threshold ratio can be 6.28. Again, the individual can have one or more symptoms of PDD or autistic disorder, or any of a number of neuromuscular or neurological symptoms.

An individual having an elevated purine level, as used herein, has one or more of an increased level of de novo purine synthesis, an increased urine level of uric acid, and a decreased level of adenine to guanine ratio in cellular assays. However, such individuals may not have an increased level of uric acid in the blood. Other methods of measuring elevated purine levels can be used.

A uridine composition is either purified uridine, a compound or product that contains uridine, a compound that increases the level of uridine in the patient, or a compound or molecule that mimics the biological function of uridine. Such a compound can be a uridine precursor or prodrug, which is processed, e.g., metabolized, degraded, or cleaved, in the body to form uridine. Such a compound can also be a uridine derivative, which includes uridine, and other molecules or compounds bound (e.g., covalently or non-covalently) to uridine, but that do not impair uridine's biological activity in patients with increased purine levels. Such compounds can also be uridine mimetics, such as other nucleotides or small molecules that have a sufficiently similar three-dimensional shape or electron configuration that the compound has at least 50 percent of the biological activity of uridine. Such compounds can also be drugs or other compounds that induce the body to produce uridine.

Uridine precursors or prodrugs include orotic acid, mono-, di- or tri-esters of uridine, including mono-, di-, and triacetyl uridine, and mono, di- or tri-phosphates of uridine including uridine monophosphate. Uridine mimetics include cytidine and mono-, di-, or tri-phosphates of cytidine including cytidine monophosphate, as well as mono-, di-, or tri-esters of cytidine including triacetyl cytidine. Deoxy-versions of these and other ribonucleosides may also be useful.

Uridine compositions also include encapsulated uridine, e.g., liposome- or polymer-encapsulated uridine. Uridine compositions also include uridine linked (e.g., covalently or non-covalently) to various antibodies, ligands, or other targeting and enveloping or shielding agents (e.g., albumin or dextrose), to allow the uridine to reach the target site (e.g., the central nervous system, muscle cells, or the peripheral nervous system) prior to being removed from the blood stream, e.g., by the kidneys and liver, and prior to being degraded.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The invention is based on the finding that individuals diagnosed with increased purine levels, e.g., individuals who also exhibit symptoms of PDD or neuromuscular disorders, can benefit from treatment by the administration of uridine and uridine analogs. Once the purine level has been determined, the patient can be easily treated by the administration of an effective amount of a uridine composition, for example, by oral or systemic intravenous administration.

Methods of Determining Elevated Purine Levels

Elevated purine levels in patients can be determined using a variety of assays. Three standard assays include measurements of: (1) uric acid or urate levels in urine; (2) de novo purine synthesis rate in fibroblast skin cells; and (3) the ratio of adenine to guanine nucleotides produced by de novo synthesis. These three assays are discussed in further detail below.

Uric Acid or Urate Levels in Urine

In children, e.g., patients who have not yet reached puberty, the urine level of uric acid is a good indicator of an elevated purine level. However, this elevation in uric acid in the urine normalizes after children reach puberty.

Urine samples should be properly pretreated, and then the level of uric acid or urate is determined using accepted standard methods, such as the uricase method described below. Each sample can be tested two or more times to assure accuracy. For example, uric acid can be measured by the uricase method on a 24 hour urine sample using the method of Liddle et al., "The Enzymatic Spectrophotometric Method for Determination of Uric Acid," J. Lab. Clin. Med., 54:903–913 (1959).

Urine samples from individuals, e.g., children suspected of having autistic disorder, are collected. These can be a single morning urine sample, or a total 24-hour collection in 50 ml polypropylene centrifuge tubes, and stored at room temperature, or refrigerated if stored more than 3 or 4 days before being assayed. The samples are later centrifuged. Solid phase extraction etc. can be used for further purification. The following is a suitable protocol for extraction of one urine sample:

(1) Urine samples are spun at 1500 rpm for 10 minutes.
(2) ~5 ml is decanted into a fresh 15 ml conical tube, and 1.6 $\mu$l of conc. HCl/ml urine is added to acidify the urine. The urine is diluted in a range of 1:100 to 3:100.
(3) 1.0 ml of diluted urine sample is added to a cuvette containing 2.0 ml of 0.1 M glycine buffer, pH 9.4.
(4) Uricase is added to catalyze the oxidation of uric acid.
(5) The resulting change on O.D. is measured at a wavelength of 292 m$\mu$ and compared to enzyme blank and reference cuvettes.

By knowing the total amount of uric acid in the cuvette, and the volume of the test solution added to the cuvette, one can determine the uric acid concentration.

Several different methods can be used to determine uric acid levels in the urine. For example, a 24-hour total urine collection sample can be used, or a single sample, e.g., a first morning urine sample, can be used. The 24-hour sample need not be normalized for urinary output, but the morning urine sample should be normalized, e.g., by a standard creatinine assay, e.g., as described in Kaufman et al., J. Pediatrics, 73:583–592 (1968). The general steps of this creatinine assay include obtaining a urine sample, placing the sample into a plastic tube containing thymol crystals to prevent bacterial growth, and storing the sample at room temperature. A modified Jaffe's reaction can be used to determine the creatinine level. Thereafter, both uric acid and creatinine levels are expressed as milligrams per 100 ml of urine and the ratio of uric acid to creatinine is calculated. Thus, the final number in the creatinine assay is the uric acid/creatinine (U/C) ratio, whereas the final number in the 24-hour sample is a measure of milligrams of urate per kilogram per day.

Based on the information described herein, the level of uric acid or urate in each sample (or the U/C ratio) is compared either to a control from one or more normal individuals of the same age or age group, or the level in the sample is compared to known, published levels in normouricosuric individuals in the same age group. An increase in the urate/uric acid level (or U/C ratio) compared to the control indicates that the patient is a candidate for the therapeutic administration of a uridine composition. For example, according to the literature, the average urate excretion level in normal individuals is about 8.3 mg urate/kg/day (Coleman et al., "Hyperuricosuria in autistic children: Does this identify a subgroup of autism?" in: Coleman (Ed.), The Autistic Syndromes, Elsevier, N.Y., 1976, pp. 183–214). The range of urate excretion in normouricosuric autistic children is from about 6.0 to about 9.0 mg urate/kg/day (Page & Coleman, Biochim. Biophys. Acta., 61913:1–6, 2000). On the other hand, the range of urate excretion in hyperuricosuric autistic children is from about 14.5 to about 35.5 mg urate/kg/day (Page & Coleman, 2000). Thus, any patients that have a urate excretion level of over 12.0 mg/kg/day, e.g., those who also have symptoms of a PDD, would benefit from the administration of a uridine composition to reduce symptoms of PDD or neuromuscular disorders.

Similarly, based on Kaufman et al. (1968), the normal range of the U/C ratio varies according to age from about 0.2 to about 3.0 for newborns, from about 0.8 to about 1.9 for two-year olds, from about 0.6 to about 1.5 for four-year olds, from about 0.6 to about 1.2 for six-year olds, from about 0.3 to about 1.4 for eight-year olds, from about 0.35 to about 1.0 for ten-year olds, and from about 0.35 to about 0.85 in 12-year olds. Thereafter, the range slowly declines for the rest of a person's life. In spite of this varying normal range, it is clear that after age twelve, the maximum range of the normal U/C ratio is about 0.8.

De Novo Purine Synthesis Rate

An elevated purine level in an individual can also be determined by assaying de novo purine synthesis. One such assay is a cell-based assay using fibroblasts taken from the patient (see, e.g., Page & Coleman, 2000). For example, fibroblasts from punch biopsies can be grown in Coon's F12 medium with 10% fetal bovine serum (FBS) in 100 mm plates. Cells are harvested in the log phase of growth between passages 6 and 10, replated at a density of $5 \times 10^5$ cells per plate, and switched to Earl's MEM with 10% dialyzed FBS. After 72 hours, the cells are harvested, replated at $10^6$ cells per plate, and 7 ml of MEM containing 10 $\mu$Ci $^{14}$C-sodium formate is added as a label. Cells are incubated for an additional 24 hours and harvested by trypsinization. The cell pellet is extracted with 0.8 M perchloric acid, precipitated protein and cell debris are removed by centrifugation at 20,000×g, and the supernatant is neutralized to pH 5–7 with 2 M potassium phosphate buffer, pH 7.5.

Labeled and unlabeled purine bases, nucleosides, and nucleotides are identified and quantified, e.g., by HPLC with continuous scintillation counting by the method of Ryll and Wagner, "Improved Ion-Pair High-Performance Liquid Chromatographic Method for the Quantification of a Wide Variety of Nucleotides and Sugar-Nucleotides in Animal Cells," J. Chromatogr., 570:77–88 (1991), in which all these compounds are quantified in a single analysis. Other similar standard methods can be used.

De novo purine synthesis can be calculated as total newly synthesized purines per total purines (normalized in some way) per day, e.g., nmol purine nucleotides synthesized+ radiolabeled purines excreted into the medium/100 nmol purines present in the cell/24 hours as previously described in Page et al., "Hypoxanthine/Guanine Phosphoribosyltransferase Variants: Correlation of Clinical Phenotype with Enzyme Activity," J. Inherit. Metab. Dis., 4:203–206 (1981).

Based on the information described herein, the level of purine synthesis in each cell sample is compared either to a control from one or more normal individuals of the same age or age group (or the average value based on the literature as discussed below), or the level in the sample is compared to the level in PDD individuals in the same age groups that have a normal purine level in the same age group. A sufficiently large increase in the purine level compared to the control indicates that the patient may benefit from the administration of a uridine composition. For example, according to the literature, the average purine level in normal individuals (and PDD individuals with a normal purine level) is about 9.0 nmol/100 nmol/day, with a range of from about 6.2 to about 10.9 nmol/100 nmol/day (Page & Coleman, 2000). The range of purine synthesis level in autistic patients with elevated purine levels is from about 23.7 to about 38.4 nmol/100 nmol/day, with an average of about 32.8 nmol/100 nmol/day (Page & Coleman, 2000). Thus, any patients that have a de novo purine synthesis level greater than about 15.0 nmol/100 nmol/day would benefit from the administration of a uridine composition to reduce symptoms associated with elevated purine levels, such as symptoms of PDD, seizures, developmental and/or behavioral problems, ataxia, and spasticity.

Adenine/Guanine Ratio

An elevated purine level in an individual can also be established by assaying the adenine/guanine nucleotide ratio. One such assay is a cell-based assay using fibroblasts taken from the patient (see, e.g., Page & Coleman, 2000). This assay provides purine synthesis information, but in cases in which the overall purine synthesis rate may be within the normal range, the ratio of adenine to guanine levels provides additional diagnostic information. In particular, if this ratio is lower than normal, the individual should benefit from the administration of a uridine composition.

The adenine to guanine nucleotide (A/G) ratio is measured by looking at the results of the de novo purine synthesis assay described above. The ratio is calculated from the amounts of radiolabeled nucleotides as (AMP+ADP+ ATP)/(GMP+GDP+GTP). For each subject three or more different incorporation experiments can be performed for improved accuracy.

Based on the information described herein, the A/G ratio in each cell sample is compared either to a control from one or more normal individuals of the same age or age group, or the ratio in the sample is compared to the ratio in PDD individuals that have a normal A/G ratio in the same age group. A decrease in the A/G ratio compared to the control indicates that the patient may benefit from the administration of a uridine composition. For example, according to accepted published criteria, the average A/G ratio in normal individuals (and PDD individuals with a normal purine level) is about 7.15, with a range of from about 6.29 to about 7.97 (Page & Coleman, 2000). The range of A/G ratios in autistic children with decreased A/G ratios is from about 4.04 to about 6.38, with an average of about 5.36 (Page & Coleman, 2000). Thus, any patients that have an A/G ratio below about 6.38 would likely benefit from the administration of a uridine composition. Since the ranges of this ratio in normal and PDD individuals overlap, a child with a ratio under 6.38 might be normal, and would thus be treated with a uridine composition only if he or she also exhibited neurological and neuromuscular symptoms. In addition, a threshold ratio of 6.28 can also be used.

General Methods of Therapy

Once a patient has been shown to have an elevated purine level using one or more of the methods described herein (or other known methods), the patient can be treated by administration of an effective amount of a uridine composition. The uridine composition can be formulated into a therapeutic composition and administered using a variety of known routes of administration.

To formulate pharmaceutical grade therapeutic compositions, the uridine composition can be purified by standard methods, e.g., filtration, to remove contaminants, if present. The final compositions can be lyophilized and resuspended in sterile, deionized water before further compounding. The therapeutic compositions can be formulated as solutions, suspensions, suppositories, tablets, granules, powders, capsules, ointments, or creams. In the preparation of these compositions, at least one pharmaceutical excipient can be included. Examples of pharmaceutical excipients include solvents (e.g., water or physiological saline), solubilizing agents (e.g., polysorbates, or Cremophor EL7), agents for achieving isotonicity, preservatives, antioxidizing agents, lactose, starch, crystalline cellulose, mannitol, maltose, calcium hydrogen phosphate, light silicic acid anhydride, calcium carbonate, binders (e.g., starch, polyvinylpyrrolidone, hydroxypropyl cellulose, ethyl cellulose, carboxy methyl cellulose, or gum arabic), lubricants (e.g., magnesium stearate, talc, or hardened oils), or stabilizers (e.g., lactose, mannitol, maltose, polysorbates, macrogols, or polyoxyethylene hardened castor oils). If desired, glycerin, dimethylacetamide, 70% sodium lactate, surfactant, or basic substances such as sodium hydroxide, ethylenediamine, ethanolamine, sodium bicarbonate, arginine, meglumine, or trisaminomethane can be added.

When the uridine composition is ingested, the excipient or carrier can be water, a flavored beverage such as a fruit juice, broth, carbonated beverage, milk, or milk shake.

Biodegradable polymers such as poly-D,L-lactide-co-glycolide or polyglycolide can be used as a bulk matrix if slow release of the composition is desired (see, e.g., U.S. Pat. Nos. 5,417,986, 4,675,381, and 4,450,150). Pharmaceutical preparations such as solutions, tablets, granules or capsules can be formed with these components. If the composition is to be administered orally, flavorings and/or colors can be added.

The new compositions can be administered via any appropriate route, e.g., intravenously, intraarterially, topically, transdermally, by injection, intraperitoneally, intrapleurally, orally, subcutaneously, intramuscularly, sublingually, nasally, by inhalation, intraepidermally, or rectally, using standard techniques.

Dosages administered in practicing the invention will depend on factors including the specific uridine composition used and its concentration in the composition, the mode and frequency of administration, the age, weight, sex, and general health of the subject, and the severity of the autistic symptoms. Suitable dosages can be determined by one skilled in the art after reviewing the present disclosure. In general, the new compositions can be administered in amounts ranging between 100 mg and 2000 mg of uridine per kilogram of body weight per day, e.g., 150, 200, 300, 400, 500, 750, 1000, 1250, 1500 or more mg/kg/day.

Dosages can be administered with meals or once, twice, or more times per day to achieve the best relief of symptoms. The dosage should be adjusted to provide a reduction in symptoms and/or to provide a normal purine level (about 6.2–10.9 nmol/100 nmol/day) as measured in, for example, the fibroblast assay described herein, and/or to provide a normal A/G ratio (about 6.29–8.0), e.g., as measured in the assays described herein. Uric acid levels in urine, and uridine blood levels can also be measured, e.g., by high-pressure liquid chromatography. These normal levels and ratios can be easily determined empirically, and the dosage administered can be slowly increased over a period of days or weeks to achieve the desired purine level. Once the proper levels or ratios are achieved, they can be easily maintained over time as required. In general, 2 to 10 $\mu$M is the normal plasma concentration of uridine, and levels of about 40 to 100 $\mu$M are in the therapeutic range.

Administration is repeated as necessary, as determined by one skilled in the art. By varying the amount of the composition or dosage, the administration protocol can be optimized based on the present disclosure to elicit a maximal improvement in symptoms, e.g., of a PDD, such as autistic disorder. Physicians, pharmacologists, and other skilled artisans are able to determine the most therapeutically effective treatment regimen, which will vary from patient to patient. The potency of a specific composition and its duration of action can require administration on an infrequent basis, including administration in an implant made from a polymer that allows slow release of the uridine.

Skilled artisans are also aware that the treatment regimen must be commensurate with issues of safety and possible toxic effect produced by the uridine or other components in the compositions. Thus, before administering the above compositions to humans, toxicity testing can be conducted in animals. In an example of toxicity testing, the uridine compositions can be administered to mice via an oral or parenteral route with varying dosages of uridine in the composition, and the mice observed for signs of toxicity using standard techniques. Of course, if the uridine composition is pure uridine, long-term experience has shown that uridine has no known toxic effects at dosages of up to 1000 mg/kg/day. Higher dosages may cause mild diarrhea in some patients. See, e.g., Leyva et al., Cancer Res., 4:5928–5933 (1984)(high dose uridine used to rescue patients from 5-fluorouracil toxicity) and Webster et al., Chapter 55, pages 1799–1837, in "The Metabolic and Molecular Bases of Inherited Disease," 7th Ed., Scriver et al. (eds.)(McGraw-Hill, Inc., New York, N.Y., 1995)(treatment of orotic aciduria with uridine, see, e.g., page 1815).

EXAMPLES

The invention is further described in the following examples, which do not limit the scope of the invention described in the claims.

Example 1

Urate Levels in the Urine of Non-Autistic and Normouricosuric Autistic Individuals Compared to Hyperuricosuric Autistic Individuals Samples of urine from normouricosuric autistic (2) and hyperuricosuric autistic (9) subjects were collected and analyzed for the presence of urate level (Page & Coleman, Biochim. Biophys. Acta., 61913:1–6, 2000). Urine samples were analyzed as follows.

Urine samples were pretreated, and then analyzed for uric acid concentration using the uricase method on a 24 hour urine sample using the method of Liddle et al., "The Enzymatic Spectrophotometric Method for Determination of Uric Acid," J. Lab. Clin. Med., 54:903–913 (1959). Each sample was tested two or more times to assure accuracy. The following protocol was used for extraction of each urine sample.

(1) Urine samples are spun at 1500 rpm for 10 minutes.
(2) ~5 ml is decanted into a fresh 15 ml conical tube, and 1.6 $\mu$l of conc. HCl/ml urine is added to acidify the urine. The urine is diluted in a range of 1:100 to 3:100.
(3) 1.0 ml of diluted urine sample is added to a cuvette containing 2.0 ml of 0.1 M glycine buffer, pH 9.4.
(4) Uricase is added to catalyze the oxidation of uric acid.
(5) The resulting change on O.D. is measured at a wavelength of 292 m$\mu$ and compared to enzyme blank and reference cuvettes.

By knowing the total amount of uric acid in the cuvette, and the volume of the test solution added to the cuvette, the uric acid concentration was determined for each sample.

These urine urate values were compared to the accepted average urate excretion level in normal individuals, which is about 8.3+/−2.0 mg urate/kg/day (Coleman et al., "Hyperuricosuria in autistic children: Does this identify a subgroup of autism?" in: Coleman (Ed.), The Autistic Syndromes, Elsevier, New York, 1976, pp. 183–214). The urate excretion in the two normouricosuric autistic children was 5.9 mg urate/kg/day (age 6) and 8.7 mg urate/kg/day (age 4). On the other hand, the urate excretion level in the nine hyperuricosuric autistic children was from 14.7 to 35.4 mg urate/kg/day. The nine patients had urate excretion levels of 14.7 (age 4), 16.2 (4), 17.9 (10), 17.9 (12), 18.1 (9), 19.8 (7), 22.4 (3), 26.5 (5), and (5).

Based on these and other data in the application, any patients that have a urate excretion level of over 12.0 mg/kg/day, e.g., those who also have symptoms of a PDD, would benefit from the administration of a uridine composition to reduce symptoms of PDD or neuromuscular disorders.

Example 2

Effect of Uridine on Patient Having Increased Uric Acid in Urine and Diagnosed with Symptoms of PDD Patient 1 was diagnosed with PDD at the age of nine. Patient 1 was treated with a low purine diet and showed some irregular improvement in symptoms of PDD. At age nine, the patient's urine was analyzed, and the urine level of uric acid was 18.1 mg/kg/day. The normal level of uric acid in normal patients at age nine is 8.3+/−2.0 mg/kg/day. After age 13, the uric acid level in the urine gradually declined to approximately normal levels, however the symptoms of PDD remained.

Between the ages of 9 and about 20, Patient 1 was treated with a variety of drugs and exercise- and stress-reducing regimens. For example, Ritalin®, Dexedrine®, and Haldol® were used with little success or worsening of his condition. The exercise- and stress-reducing regimen helped in some respects, because Patient 1 was often fatigued. In addition, the low purine diet was continued at times along with vitamin B6 and magnesium. Over these many years, and between the ages of 20 and 31, Patient 1 had varying levels of rather minor improvements in his symptoms in response to these and other attempted therapies.

At age 31, Patient 1 began use of uridine, with an oral dosage of approximately 50 mg/kilogram of body weight per day. The dosage level was increased to 150 mg/kg/day, and Patient 1 obtained rapid benefits of this dosage of uridine as shown in Table 1, which shows comparative narrative data. The improvements declined or regressed upon cessation of uridine therapy and were also dosage-dependent. In particular, Patient 1 tried varying dosages of uridine up to 1000 mg/kg/day. The higher dosages gave the most improved results.

TABLE 1

| No Uridine | With Uridine |
| --- | --- |
| Motor skills: | Motor skills: |
| 1. Gross motor skills: | 1. Gross motor skills: |
| a. Walk-clumsy, veered from side to side. | a. Walk-far smoother. Looks normal when he walks. |
| b. Moving through space-hit furniture, could not stop movements, e.g., would often crash against the front door because he could not stop running or walking. | b. Does not crash into furniture, does not smash into front door. Has been able to learn how to dance. |
| c. Sitting down-very awkward, would face the seat, put hands down, then semi-crawl into seat. | c. Sits down normally, is able to feel the seat with the back of his legs, and to lower his body to sitting. |
| d. Hugging-would hug so hard that he would hurt others, found it hard to let go when asked. | d. Hugs normally-finds it easier to be touched by others, can release when asked. |
| e. Often felt exhausted at end of day because of the effort of trying to move more naturally. | e. Much less exhaustion and pain at the end of the day. |
| f. Could not judge "social" distance-usually stood or sat too closely to others. | f. Able to judge "social distances" appropriately which has improved his social interactions markedly. |
| g. Could not find parts of his own body (he knew the names on a diagram, but could not point to his shoulders, knees, etc.). | g. He is now able to find his body parts. This is one of the most amazing changes; we have worked for years on this issue without success. |
| 2. Fine motor: | 2. Fine motor: |
| a. Unable to use a screwdriver. | a. Able to use a screwdriver and other tools. |
| b. Very poor laboratory skills; needed others to manipulate the equipment. | b. Able to perform experiments on his own. Manipulated micro-pipettes and performed electrophoresis. |
| c. Made low "C's" or could not complete laboratory classes. Speech and Language: | c. Made "A's" in advanced laboratory courses demanding excellent small motor control. Speech and Language: |
| 1. Speech often jumbled. | 1. Speech rarely jumbled, speaks logically, syntactically correctly, and with excellent syntactically correctly, and with excellent vocabulary. |
| 2. Great difficulty processing language. | |
| a. Misunderstood much of what was said, needed several repetitions. | |
| b. Very slow to understand jokes. | |
| c. Rarely able to participate in repartee. | |
| d. Difficulty having normal back and forth conversation. | 2. Great improvement in processing language. |
| e. Often did not make eye contact. Cognitive Performance | a. Understands easily, rarely needs repetitions. |
| 1. Reading: | b. Very quick to understand jokes, (often the first one to laugh). |
| a. Very slow, needed to reread repeatedly to comprehend, depended on talking books plus text, whenever possible. | c. Able to engage in repartee, is more and more frequently responding with quick, funny remarks. |
| b. Process so difficult that it was hard to maintain focus. | d. Engages in normal back and forth conversation. |
| 2. Writing: needed assistance on all assignments-most assignments were late. | e. Usually makes eye contact. Cognitive Performance |
| 3. Spatial reasoning: could not visual three dimensional models of molecules-had to learn by trying to make concrete model. | 1. Reading: a. Able to read smoothly at first pass through. (We have noticed a very marked change in oral reading). |
| 4. Creativity: Very creative, with ability to integrate ideas-many new ideas but not able to communicate them. | b. Able to sit and read 50 pages of advanced biochemistry textbook in three hours-with complete comprehension. |
| 5. Flexibility of thinking: minimal. | c. Has also started reading for fun. |
| 6. Could only complete 9 to 12 units a semester. These units were often repetitions of previous courses. Never able to complete by end of semester. Struggled to make B's and C's. Usually had at least one incomplete that would then be carried into the next semester. | 2. Wrote all lab reports and literature reviews independently-no editing. Made A's on assignments. All assignments turned in on time. 3. Spatial reasoning: can visualize three dimensional models, can visualize rotations of models and analyze interactions of models in three dimensions. 4. Creativity: Still creative. However, he is absorbing so much new information easily, and he is able to convey his thinking clearly that to others he appears suddenly to be "creative." 5. No longer rigid, can hear different viewpoints, can adapt his own thinking. 6. Took 16 units a semester, all new material, advanced biochemistry, lab courses, molecular biology, etc.-competing against regular students. Often made the top scores in the class. |

As demonstrated in the table, Patient 1's neurological and neuromuscular symptoms (e.g., symptoms of both autistic disorder and ataxia) improved dramatically upon administration of uridine.

Other Embodiments

The data described herein indicate that elevated purine levels are caused by a metabolic error in one of the enzymes related to purine nucleotide interconversion. The specific enzyme defect responsible for increased de novo purine synthesis is likely an excess of adenosine monophosphate (AMP) deaminase activity. Accordingly, AMP deaminase activity can be used as another diagnostic test for elevated purine levels associated with various PDD disorders. In addition, AMP deaminase can be inhibited using specific inhibitors such as deoxycoformycin, a known anti-cancer drug.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating an individual having an elevated purine level, the method comprising administering to the individual an effective amount of a uridine composition.

2. A method of claim 1, wherein an effective amount of the uridine composition provides about 100 to 1500 mg of uridine/kg of body weight/day.

3. A method of claim 1, wherein an effective amount of the uridine composition provides about 100 to 250 mg of uridine/kg of body weight/day.

4. A method of claim 1, wherein an effective amount of the uridine composition is administered orally.

5. A method of claim 1, wherein the individual has one or more symptoms of Pervasive Developmental Disorder (PDD).

6. A method of claim 1, wherein the individual has one or more symptoms of autistic disorder.

7. A method of claim 1, wherein the individual has seizures.

8. A method of claim 1, wherein the individual has one or more symptoms of a neuromuscular disorder.

9. A method of claim 1, wherein the patient has ataxia.

10. The method of claim 1, wherein the uridine composition comprises uridine and a liquid ingestible carrier.

11. The method of claim 1, wherein the uridine composition comprises triacetyl uridine.

12. The method of claim 5, wherein the amount of the uridine composition is effective to improve one or more of the symptoms of PDD.

13. The method of claim 6, wherein the amount of the uridine composition is effective to improve one or more of the symptoms of autistic disorder.

* * * * *